United States Patent
Deckwer et al.

(10) Patent No.: US 6,878,545 B2
(45) Date of Patent: Apr. 12, 2005

(54) METHOD FOR SEPARATING VIABLE CELLS FROM CELL SUSPENSIONS

(75) Inventors: Wolf-Dieter Deckwer, Braunschweig (DE); Ricardo De Andrade Medronho, Braunschweig (DE); Birger Anspach, Braunschweig (DE); Marc Luebberstedt, Braunschweig (DE)

(73) Assignee: Gesellschaft fuer Biotechnologische Forschung mbH (GBF), Braunschweig (DE)

( * ) Notice: Subject to any disclaimer, the term of this patent is extended or adjusted under 35 U.S.C. 154(b) by 204 days.

(21) Appl. No.: 10/275,086

(22) PCT Filed: Mar. 30, 2001

(86) PCT No.: PCT/EP01/03665

§ 371 (c)(1),
(2), (4) Date: Mar. 25, 2003

(87) PCT Pub. No.: WO01/85902

PCT Pub. Date: Nov. 15, 2001

(65) Prior Publication Data

US 2003/0166269 A1 Sep. 4, 2003

(30) Foreign Application Priority Data

May 11, 2000 (DE) .......................................... 100 22 635

(51) Int. Cl.$^7$ ................................................. C12N 5/00
(52) U.S. Cl. .................... 435/366; 435/348; 435/372.2; 435/374; 435/261; 209/725; 209/729; 209/734; 210/788
(58) Field of Search .................................. 435/366, 374, 435/348, 372.2, 261; 209/725, 734, 729; 210/788

(56) References Cited

U.S. PATENT DOCUMENTS

| | | | |
|---|---|---|---|
| 453,105 A | * 5/1891 | Bretney | 210/512.1 |
| 3,647,633 A | 3/1972 | Dawson | |
| 4,329,433 A | * 5/1982 | Seebeck et al. | 435/162 |
| 4,446,066 A | * 5/1984 | Luijerink | 530/380 |
| 5,141,763 A | * 8/1992 | Hansen et al. | 426/464 |
| 5,547,858 A | 8/1996 | Nagano et al. | |
| 6,146,525 A | * 11/2000 | Li et al. | 210/221.2 |
| 2002/0160022 A1 | * 10/2002 | Schasteen et al. | 424/269.1 |

FOREIGN PATENT DOCUMENTS

| | | |
|---|---|---|
| EP | 0 068 537 A | 1/1983 |
| WO | WO 92/01779 A | 2/1992 |
| WO | WO98/01394 A | 1/1998 |

OTHER PUBLICATIONS

Database WPI, Section Ch, Week 199209. Derwent Publications Ltd., London, GB; Class D16. AN 1992–070901 XP002176099 & SU 1 637 882 A (Moscow Chem Equip Inst), Mar. 30, 1991, Zusammenfassung.

* cited by examiner

Primary Examiner—Leon B. Lankford, Jr.
(74) Attorney, Agent, or Firm—Frommer Lawrence & Haug LLP; Ronald R. Santucci

(57) ABSTRACT

The invention relates to a method of separating viable cells from cell suspensions using hydrocyclones, which method can, especially, be carried out continuously.

5 Claims, 4 Drawing Sheets

METHOD FOR SEPARATING VIABLE CELLS FROM CELL SUSPENSIONS

This application is a 371 of PCT/EP01/03665 filed on Mar. 30, 2001, published on Nov. 15, 2001 under publication number WO 01/85902 A1 and claims priority benefits of German patent application, DE 100 22 635.3 filed May 11, 2000.

The invention relates to a method of separating viable cells from cell suspensions using hydrocyclones.

A list of the literature sources referred to in the following description of the prior art, with more precise bibliographic details, is located at the end of this description.

In the past decades, cell culture technology has made great advances and has, in particular, contributed to the production of high-quality products of therapeutic benefit, such as pharmaceutical proteins of a very great variety. New impetuses are currently based on tissue cultivation and on the direct use of cells and genes for therapy. Great commercial benefit is expected here (Peshwa, 1999). However, it has been found, when working up cell cultures, that a simple method of separating viable cells, or of increasing their concentration, is not available.

Many bioreactors used in industry for producing biopharmaceutical products have a so-called perfusion mode of operation. In that method, cell-free culture medium is continuously drawn off from the reactor while replenishment with fresh medium is simultaneously carried out. Using that mode of operation, there are obtained high cell concentrations and also, therefore, high volumetric productivities for the desired pharmaceutical products, compared to intermittent or batch operation and fedbatch cultures (Zeng & Deckwer, 1999).

For harvesting a mammalian cell culture, whatever the mode of operation used, the first necessary step is separation of the cells from the medium. The conventional methods of achieving that objective are centrifugation, microfiltration and settling out under the earth's gravity.

Disadvantages of the use of centrifuges are their high purchase costs, the high operating costs and their relatively small capacity. The use of centrifuges in mammalian cell perfusion culture therefore results in increased investment and operating costs, which is ultimately reflected in the end product price. A further disadvantage of centrifuges is the difficulty of their sterilisation and of aseptic or monoseptic operation.

That is true of, especially, disc centrifuges, which are most frequently used for the purpose of cell separation. In addition to in situ sterilisation, the generation of heat during operation of disc centrifuges is a further problem.

Those problems can, however, be successfully solved, as shown by a patent of Zentritech (Yhland, 1992), wherein plastic bags are used, which can be inserted into the rotor of the centrifuge and which can be applied to the fermentation system without rotating seals. The design and operation of the Zentritech system are, however, very complicated, and it has a comparatively low capacity and involves high costs.

With respect to microfiltration, the main problem therein is that the membrane becomes coated and, as a consequence thereof, blocked during operation when filtrate is drawn off continuously. This means that the cell separation process cannot be operated stably over a relatively long period of time, more specifically for a period of several months, which is, however, necessary in the case of mammalian cell perfusion cultures if used for production of pharmaceutical proteins.

In order to avoid the problem of blockage of the membrane, rotary filters have been proposed. An overview of such apparatuses can be found in Tokashiki and Yokoyama (1997). However, the authors also emphasise that it is scarcely possible for soiling or blockage of the membrane to be avoided completely.

A further important problem in the use of filtration separating techniques by means of membranes is their low mechanical stability, which can result in them breaking, especially when high transmembrane pressures are present. In such a case, the entire process must be shut down and at least the membrane replaced, if not the entire process abandoned because of microbial contamination.

The dynamic filter proposed by, and patented for, GBF (Gesellschaft für Biotechnologische Forschung mbH) has a conical rotor, which suppresses cell deposition at the membrane surface, but even in this case blockage and the problem of membrane breakage cannot be avoided longterm (Kroner & Vogel 1998).

In the case of the sedimentation of mammalian cells under the earth's gravity, only very low settling speeds are obtained, even in the case of relatively large cells, such speeds being merely in the range from 2 to 10 cm/h, so that cell separability is, in this case, only very low (Tokashiki & Yokoyama, 1997). Because of the low settling speed of the cells, the perfusion rate must be kept low in view of the small settling area in the reactors conventionally used. High perfusion rates can be achieved only in reactors having extremely large settling areas, which causes major problems when scaling-up the reactors and also when sterilising them. Settling under the earth's gravity is therefore of low importance for perfusion systems.

New methods of cell separation have recently been published, these being, on the one hand, ultrasound-enhanced sedimentation (Hawkes et al., 1997) and, on the other hand, dielectrophoretic separation (Doscoslis et al., 1997). These methods are, however, still under development. In addition, they are relatively complex and, from an economic standpoint, are hardly capable of competing with the conventional methods of cell separating or cell concentrating already described.

There is accordingly an urgent need for a method of increasing the concentrations of cells in perfusion cultures and also, in general, of harvesting cell cultures. Ideally the device or apparatus used to carry out the method should of simple construction, have a low personnel requirement, be robust in operation and simple to scale-up.

The problem of the invention is to overcome the problems associated with the described prior art and to meet the resulting urgent need for an alternative method of separating viable cells from cell suspensions.

In accordance with the invention there is accordingly made available, according to patent claim 1, a method of separating viable cells from cell suspensions, wherein the cell suspension is introduced, by way of an inlet device, tangentially into the cylinder space of at least one hydrocyclone and is allowed to flow in a downwardly directed, spirally circling course through the cone of the hydrocyclone, a suspension of increased cell concentration being collected at the bottom run-off outlet device of the hydrocyclone, located at the bottom end of the cone, and a suspension of decreased cell concentration being collected at the top run-off outlet device, which is arranged centrally in, and extends into, the cylinder space, and the pressure drop between the inlet device and the top run-off outlet device being at most 4 bar, preferably 2 bar.

Using the method according to the invention, it is possible to obtain, in the bottom run-off from the hydrocyclone, even in the case of a singular arrangement, an increase in concentration of at least 1.2 times the cell count in the inlet, without appreciably impairing the viability of the cells.

The method according to the invention is accordingly suitable, in particular, for use with continuous cell cultures having cell return, as a result of which high cell densities and productivities can be achieved for proteins (pharmaceutical proteins, diagnostic agents, monoclonal antibodies). In addition, it is possible by this means to replace more complicated perfusion reactor systems, for example having membrane technology, as a result of which, overall, operation becomes more robust and sterilisability more reliable.

Further advantageous and/or preferred embodiments of the invention are contained in the subject-matter of the subordinate claims.

In a further embodiment of the method according to the invention, a plurality of identical or different hydrocyclones arranged in parallel or in series are accordingly operated discontinuously or continuously.

The cells that are separated from cell suspensions, or whose concentration is increased, by the method according to the invention are, for example, mammalian cells, such as blood cells or hybridoma cells, or insect cells.

In the Figures.

The invention is described in greater detail hereinbelow, without limitation, on the basis of exemplary embodiments and with reference to the Figures.

Hydrocyclones per se are well known to the person skilled in the art, and the principles of their operation are described in detail in manuals and textbooks (Bradley, 1965; Svarovsky, 1984; Heiskanen, 1993). Because they are of simple arrangement and construction, they have low prices compared to other apparatuses that fulfil the same function. With respect to their applications, cyclones are extremely versatile. They can be used for concentrating suspensions, for clarifying liquids, for sorting solids by size and density, for separating immiscible liquids, for degassing liquids etc. There are numerous hydrocyclone manufacturers such as, for example, Dorr-Oliver Inc., Krebs Engs. in the USA, Richard Mozley Ltd in England, and AKW, Apparate und Verfahren GmbH in Germany to name but a few.

Figure 1:
FIG. 1 shows, in principle, the structure of a hydrocyclone used in the method according to the invention.

As illustrated by way of example in FIG. 1, hydrocyclones consist of a conical portion of, in itself, any length and any diameter, which is followed by a short cylindrical portion provided with an inlet device, for example an appropriate pipe, for tangentially introducing the material to be separated. The cylinder is closed with a plate, axially in the middle of which the top run-off takes place, for example by means of an appropriate outlet device, which extends into the cylinder space, for example a cylindrical pipe or a pipe connection. That central top run-off outlet device is also called a vortex finder or dip tube. The cone ends in an outlet device, for example a cylindrical pipe, by way of which the bottom run-off flows away. That bottom run-off outlet device may be provided with a controllable valve.

Although the first patent for cyclones is already more than 100 years old (Bretnei, 1891), the first industrial application came only at the end of the Second World War. The apparatus, which was originally designed to achieve solid/liquid separations, is currently also used for solid/solid (Klima & Kim, 1998), liquid/liquid (Moraes et al., 1996) and gas/liquid separations (Marti et al., 1996).

Figure 2:
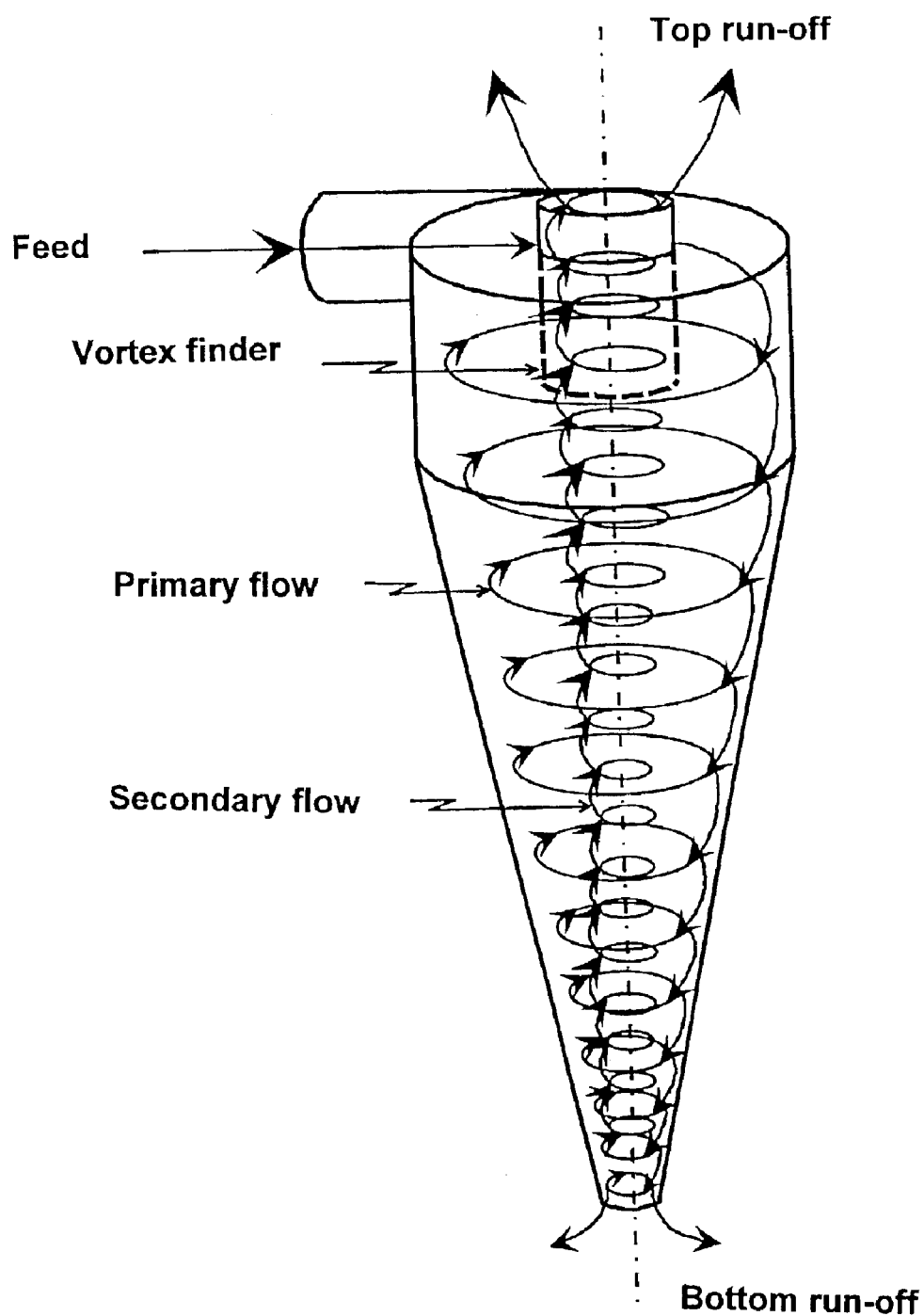
FIG. 2 shows the mode of operation of a hydrocyclone used in the method according to the invention.

The mode of operation of a hydrocyclone used in the method according to the invention can be seen from FIG. 2. The expression "feed" refers to a cell suspension, which enters the hydrocyclone tangentially through the inlet pipe. The feed can originate from a biological reactor or any other source of cells. The expression "bottom run-off" refers to the suspension of increased cell concentration, which leaves the hydrocyclone at the end of the conical taper. The expression "top run-off" refers to the suspension liquid of decreased cell concentration, which leaves the cyclone at the top by way of the concentric pipe.

Advantageously, two or more identical or different hydrocyclones arranged in series may be operated in the method according to the invention, as described, for example, in Chapter 9 of the book by Svarovsky (1984) ("hydrocyclones in series" and "series of hydrocyclones"). An arrangement of two or more hydrocyclones in series or in sequence is achieved, for example, by means of the fact that the top run-off of the first hydrocyclone becomes the inlet of the second etc. Of course, an additional device such as, for example, a pump may also be accommodated in the connecting lines between the two hydrocyclones in question.

In the method according to the invention, the parallel arrangement of two or more hydrocyclones is also advantageous. Such parallel operation is already much used in industry and is described very specifically, for example, in Chapter 5 of the above-mentioned book (Svarovsky, 1984) ("hydrocyclones in parallel"). An arrangement of two parallel hydrocyclones would be provided, for example, by separating the feed into two portions, with each of those portions being fed directly into a hydrocyclone.

In contrast to centrifugation, the separation principle of which is based on the sedimentation caused by the centrifugal force occurring in the rotors, hydrocyclones do not require rotors of that kind, because the vortex motion is caused by the liquid itself, as can be seen from FIG. 2.

As a result of the tangential introduction of the feed (for example, cell suspension whose cell concentration is to be increased) into the upper part of the cylindrical portion, the liquid (for example, cell suspension whose cell concentration is to be increased) undergoes a vigorous, downwardly directed, vortex motion, as a result which there is also produced a pronounced centrifugal field. As a result of that centrifugal field, the solid particles (for example, cells) travel outwards towards the wall and are guided downwards by the conical taper and finally taken off by way of the bottom run-off outlet. The liquid (for example, the cell suspension of decreased cell concentration), in contrast, reverses its vertical direction and moves upwards with an even more vigorous vortex motion and leaves the hydrocyclone through the top run-off outlet. This liquid retains only relatively small or relatively light particles.

Finally, the difference in the static pressure between the inlet and outlet pipe causes the vortex motion, the settling in the centrifugal field produced and the increase in concentration of the particles (for example, cells) in the bottom run-off and their decrease in concentration in the top run-off.

The conventional area of use of hydrocyclones is the concentration of suspensions, wherein the large-size particles leave the apparatus as a bottom run-off in the form of a concentrated suspension, whereas the fine particles, which cannot be separated, leave through the top run-off in the form of a diluted suspension.

In the past, the view was held that hydrocyclones cannot be used effectively for concentrating suspensions when the density difference between the particles and the suspending liquid is <0.5 g/cm$^3$. Thew (1983) was the first to refute that view, patenting a hydrocyclone for liquid/liquid separation, for example oil dispersed in water, the density difference between the water and the oil drops being in the range of only from 0.1 to 0.2 g/cm$^3$.

Mammalian cells, insect cells, plant cells and microorganisms are small, and their density is close to that of water, being typically about 1.05 g/cm$^3$. For that reason, the view exists in the prior art that it is not possible to separate those cells from aqueous cell suspensions using hydrocyclones. As an example of that (erroneous) view, there may be quoted here a written observation by Naganna et al. (1996) in their patent: "When a solution containing cells is fed to the liquid cyclone, the cells have a diameter smaller than the critical diameter so that there is no difference in concentration between the upstream and the downstream in the liquid cyclone, which makes separation of the cells impossible".

However, as the Examples hereinbelow illustrating the present invention show, that view is not correct. The invention is based on the finding that hydrocyclones can be used very well for separating cells from aqueous cell suspensions with high separating efficiency, that being the case without impairing cell viability to any practically relevant extent.

Another, frequently expressed view is that mammalian cells are highly sensitive to shear. In accordance with the invention, it has, however, been found that mammalian cells and similar cells withstand shear effects well, especially those occurring in hydrocyclones, provided that a certain critical pressure difference or a certain critical pressure drop (manometric pressure in each case) between the inlet device and the top run-off outlet device in the cylindrical portion of the hydrocyclone (about 4 bar, preferably 2 bar) is not exceeded. This is certainly connected in part to the fact that the dwell time of the cells in the hydrocyclone is extremely short.

In accordance with the method of the invention, a cell suspension coming directly from the bioreactor is fed under pressure, for example up to 4 bar, preferably 2 bar, above atmospheric pressure, to one or more (that is to say, parallel-arranged) hydrocyclones. The hydrocyclones used can be of a conventional mode of construction. For example, the commercially manufactured hydrocyclones from Dorr-Oliver Inc., as described in Chapter 10 of Bradley's book (Bradley, 1965), are suitable.

Although commercially available hydrocyclones, for example those made by the manufacturers mentioned hereinbefore, are preferably used in accordance with the invention, there are in general no particular limitations in respect of construction or type. Suitable hydrocyclones can be determined by the person skilled in the art by means of simple tests and taking into account practical circumstances. The only critical aspect is that the intended objective is achieved, namely the separation of viable cells from cell suspensions. For example, hydrocyclones having approximately the following features of construction are suitable.

The length of the cylindrical portion is approximately 2 to 12 mm and its diameter approximately 5 to 15 mm, preferably 10 mm. The angle at which the conical portion tapers, starting from the cylindrical portion, is in the range from approximately 5 to 20°, which simultaneously determines the length of the conical portion. The inlet device (for the cell suspension) into the cylindrical portion, for example an appropriate pipe, has, for example, a diameter in the range from approximately 0.5 to 4 mm, preferably 2 mm. The top run-off outlet device, for example an appropriate pipe (dip tube), has, for example, a diameter of 1 to 5 mm and extends, for example, approximately 1 to 6 mm into the cylindrical portion. The bottom run-off outlet device, for example an appropriate pipe, has, for example, a diameter of 0.5 to 7 mm.

The feed (that is to say the cell suspension whose cell concentration is to be increased) is introduced tangentially into the cylindrical portion of the hydrocyclone, as a result of which a vigorous, downwardly directed vortex motion and, as a result thereof, a centrifugal field are produced, by virtue of which the cells are transported radially outwards, reaching the wall and leaving the hydrocyclone as the bottom run-off. The bottom run-off line is so selected or comprises a shut-off device, for example a controllable valve by means of which the bottom run-off can be controlled, that a portion of the liquid stream reverses its vertical direction and, under even more vigorous vortex formation, is taken off at the top through the central top run-off line, also carrying relatively small particles and cell fragments out with it. In contrast, the concentration of cells in the bottom run-off is increased.

The method according to the invention of separating cells from cell suspensions can of course not only be used in conjunction with perfusion cell cultures and for the harvesting of cells, but is in general suitable for any separation problem for which the use of a hydrocyclone is advantageous. The hydrocyclones used can be operated continuously, but also with interruptions, that is to say discontinuously. The precise selection of the hydrocyclone size is important for obtaining a high separation effect (features of construction of the individual hydrocyclone parts are given hereinbefore by way of example). The viability of the cells is generally unimpaired provided that the critical pressure drop already mentioned hereinbefore is not exceeded.

In the method according to the invention it is also possible to use a plurality of hydrocyclones, which may be arranged or connected in series or in parallel. Connection in series can be used to increase the separating efficiency or separation effect, that is to say in order to achieve a greater concentration of cells in the bottom run-off.

The separation, in accordance with the invention, of cells from cell suspensions using hydrocyclones has pronounced advantages over separation using centrifuges. Hydrocyclones are simple to manufacture and, as a result thereof, can be obtained at low prices.

Installation of the hydrocyclones is simple and economical, because no special constructional measures are necessary and only an extremely small installation area is required. Maintaining the hydrocyclones in an operational state is simple because they contain no moving parts.

The speed of flow is, compared to their size, many times greater and the dwell time of the cells is correspondingly low. As a result, the use of hydrocyclones for harvesting cell cultures can be expected to reduce investment costs as well as operating costs, which will also be reflected in a lower product price.

These advantages are also valid when membrane filters and settlers are used for comparison. Compared to membrane filters, hydrocyclones have the additional advantage that a constant stream or flow speed or rate can be set for a given pressure drop in simple manner and their operation is possible for months, possibly even years, without interruption.

The following Examples illustrate the invention without limiting it.

EXAMPLE 1

Figure 3:
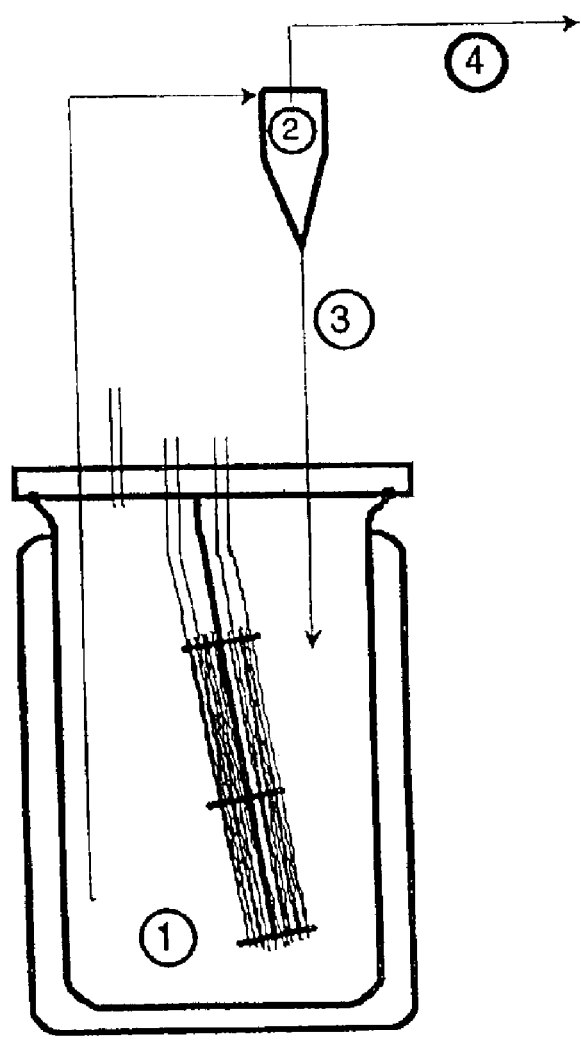
FIG. 3 shows the combination of a hydrocyclone used in the method according to the invention with a bioreactor.

In the arrangement shown in FIG. 3, the bioreactor 1 was used to cultivate HeLa cells. 95.4% of the cells in the suspension were viable, and the cell suspension was fed to a Doxie hydrocyclone 2, manufactured by Dorr-Oliver Inc. The selected pressure drop resulted in a flow speed of 36.7 cm$^3$/s, and it was possible to separate off in the bottom run-off 3 80% of the cells, of which 95.2% were viable. The initial cell concentration was 0.43% by volume; the cell concentration obtained in the bottom run-off was 0.7% by volume and the cell concentration in the top run-off (4) was only 0.19% by volume, wherein 96.7% of the cells were viable.

Performing the same experiment using a hydrocyclone of the same size as the Doxie hydrocyclone but of different geometric dimensions, manufactured by Richard Mozley Ltd., resulted in a higher flow speed or flow rate, namely 50 cm$^3$/s, but with lower cell retention in the bottom run-off, namely only 40%. This means that it is not only the size of the hydrocyclone that is important for good separation but also its geometric dimensions.

EXAMPLE 2

Figure 4:
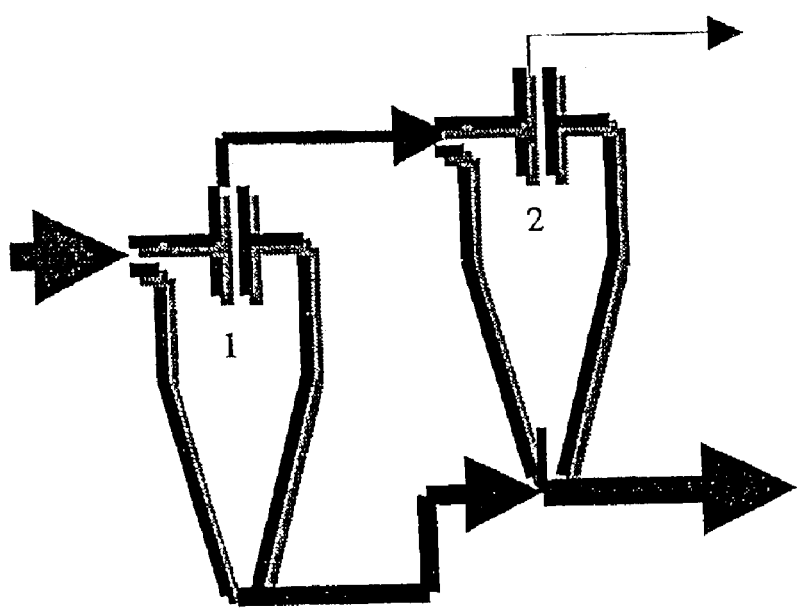
FIG. 4 shows the combination of two hydrocyclones used in the method according to the invention, for operation in series.

The hydrocyclones, for example Doxie hydrocyclones, can also be used arranged in series, as shown in FIG. 4. A suspension of HeLa cells, of which 87.2% were viable, was fed to the first hydrocyclone 1, the top run-off of which was passed, as the feed, to the second Doxie hydrocyclone 2. In the case of the selected pressure drop, it was possible to concentrate a total of 94% of the cells in the bottom run-off from the first and second hydrocyclones, the cell viability being 89%.

In summary, the invention accordingly relates to a new method of separating viable cells from cell suspensions, for example biological culture media, with the aid of hydrocyclones, the cells being preferably higher cells, that is to say cells of mammals, for example hybridomas etc., or cells of insects, which can, by means of the method according to the invention, be separated or concentrated (harvested) with a high separating or concentrating effect whilst substantially preserving cell viability. Compared to other devices and apparatuses, such as particular centrifuges and membrane filters in crossflow operation, which can fulfil the same function, the hydrocyclones are simple, cheap, reliable and robust devices. Replacing known separation and cell-retention systems by hydrocyclones reduces the use of capital and the operating costs. The method according to the invention using hydrocyclones can, in particular, be used for cell retention in perfusion cultures.

Literature Sources

Bradley, D. (1965) The Hydrocyclone. Pergamon Press, Oxford.

Bretnei, E., U.S. Pat. No. 453,105 (1891).

Colman, D. A. and Thew, M. T. (1980), Cyclone separator, U.S. Pat. No. 4,237,006.

Doscolis, A., Kalogerakis, N., Behrie, L. A. and Kaler, K. V. I. S. (1997), Filter for perfusion cultures of animal cells and the like. U.S. Pat. No. 5,626,734.

Hawkes, J. J., Limaye, M. S. and Coakley, W. T. (1997), Filtration of bacteria and yeast by ultrasound-enhanced sedimentation. Journal of Applied Microbiology, 82 (1), 39–47.

Heiskanen K (1993) Particle Classification. Chapman & Hall, London.

Klima M S & Kim B H (1998) Dense-medium separation of heavy-metal particles from soil using a wide-angle hydrocyclone. Journal of Environmental Science and Health, Part A. 33: 1325–1340.

Kroner, K.-H. and Vogel, J. (1998). European Patent No. EP-0 815 927 A2.

Marti S, Erdal F M, Shoham O, Shirazi S & Kouba G E (1996) Analysis of gas carry-under in gas-liquid cylindrical cyclones. In: Claxton D, Svarovsky L & Thew M (eds.) Hydrocyclones '96 (pp. 399–421) Mechanical Engineering Publications, London & Bury Saint Edmunds.

Moraes C A C, Hackenburg C M, Russo C & Medronho R A (1996) Theoretical analysis of oily water hydrocyclones. In: Claxton D, Svarovsky L & Thew M (eds.) Hydrocyclones '96 (pp. 383–398) Mechanical Engineering Publications, London & Bury Saint Edmunds.

Naganu, Y., Suganuma, T, Satoh, K. and Ikeda, M. (1996), Method for purification of amino acids, nucleic acids using a hydrocyclone. U.S. Pat. No. 5,547,858.

Peshwa, M. V. (1999), Mammalian Cell Culture. In. Demain, A. L. and Davies, J. E. (eds.) Manual of Industrial Microbiology and Biotechnology, $2^{nd}$ Ed., ASM Press, Washington.

Svarovsky L (1984) Hydrocyclones. Holt, Rinehart and Winston, London.

Tokashiki, M. and Yokoyama, S. (1997), Bioreactors designed for animal cells. In: Hauser, H. and Wagner, R. (eds.), Mammalian Cell Biotechnology in Protein Production, Walter de Gruyter, Berlin.

Yhland, C. (1992), Centrifugal Separator. U.S. Pat. No. 5,160,310.

Zeng, A.-P. and Deckwer, W.-D. (1999), Model simulation and analysis of perfusion culture of mammalian cells at high cell density. Biotechnology Progress, 15, 373–382.

What is claimed is:

1. Method of separating viable mammalian or insect cells from cell suspensions, wherein the cell suspension is introduced, by way of an inlet device, tangentially into the cylinder space of at least one hydrocyclone and is allowed to flow in a downwardly directed, spirally circling course through the cone of the hydrocyclone, a suspension of increased cell concentration being collected at the bottom run-off outlet device of the hydrocyclone, located at the bottom end of the cone, and a suspension of decreased cell concentration being collected at the top run-off outlet device, which is arranged centrally in, and extends into, the cylinder space, and the pressure drop between the inlet device and the top run-off outlet device being at most 4 bar, the hydrocyclone having the following features of construction:

cylindrical portion:

length 2 to 12 mm diameter 5 to 15 mm conical portion:

angle of taper 5 to 20° inlet device:

diameter 0.5 to 4 mm top run-off outlet device:

diameter 1 to 5 mm depth of introduction 1 to 6 mm bottom run-off outlet device:

diameter 0.5 to 7 mm.

2. Method according to claim 1, wherein the pressure drop between the inlet device and the top run-off outlet device is 2 bar.

3. Method according to claim 2, wherein the hydrocyclone has the following features of construction:

cylindrical portion:

length 2 to 12 mm
diameter 10 mm
conical portion:
angle of taper 5 to 20°
inlet device:
diameter 2 mm
top run-off outlet device:
diameter 1 to 5 mm
depth of introduction 1 to 6 mm
bottom run-off outlet device:
diameter 0.5 to 7 mm.

4. Method according to claim 1, wherein a plurality of identical or different hydrocyclones arranged in parallel or in series are operated discontinuously or continuously.

5. Method according to claim 1, wherein the mammalian cells are blood cells or hybridoma cells.

* * * * *